United States Patent
Mazumder et al.

(10) Patent No.: US 11,596,328 B2
(45) Date of Patent: Mar. 7, 2023

(54) METHOD AND SYSTEM FOR POSTURAL STABILITY ASSESSMENT

(71) Applicant: Tata Consultancy Services Limited, Mumbai (IN)

(72) Inventors: Oishee Mazumder, Kolkata (IN); Kingshuk Chakravarty, Kolkata (IN); Debatri Chatterjee, Kolkata (IN); Aniruddha Sinha, Kolkata (IN); Abhijit Das, Haridevpur (IN)

(73) Assignee: Tata Consultancy Services Limited, Mumbai (IN)

( * ) Notice: Subject to any disclaimer, the term of this patent is extended or adjusted under 35 U.S.C. 154(b) by 508 days.

(21) Appl. No.: 15/914,286

(22) Filed: Mar. 7, 2018

(65) Prior Publication Data
US 2019/0008417 A1    Jan. 10, 2019

(30) Foreign Application Priority Data
Jul. 7, 2017    (IN) .............................. 201721024012

(51) Int. Cl.
*A61B 5/11*    (2006.01)
*A61B 5/00*    (2006.01)
(Continued)

(52) U.S. Cl.
CPC .......... *A61B 5/1116* (2013.01); *A61B 5/1122* (2013.01); *A61B 5/1123* (2013.01);
(Continued)

(58) Field of Classification Search
CPC ... A61B 5/1116; A61B 5/1128; A61B 5/4561; A61B 5/7264; A61B 5/1122;
(Continued)

(56) References Cited

U.S. PATENT DOCUMENTS

| | | |
|---|---|---|
| 9,451,916 B2 | 9/2016 | Curtiss |
| 2017/0000383 A1 | 1/2017 | Brown et al. |

(Continued)

OTHER PUBLICATIONS

Chakravarty et al. (2016). Quantification of balance in single limb stance using kinect. 854-858. 10.1109/ICASSP.2016.7471796. (Year: 2016).*

(Continued)

*Primary Examiner* — Devin B Henson
*Assistant Examiner* — Justin Xu
(74) *Attorney, Agent, or Firm* — Finnegan, Henderson, Farabow, Garrett & Dunner, LLP

(57) ABSTRACT

This disclosure relates generally to health monitoring and assessment systems, and more particularly to perform postural stability assessment of a user and quantify the assessed postural stability. In an embodiment, the system, by monitoring specific actions (which are part of certain tests done for the postural stability assessment) being performed by a user, collects inputs which are then processed to determine SLS duration, the body joint vibration, and the body sway area of the user, while performing the tests. By processing the SLS duration, the body joint vibration, and the body sway area together, a postural stability index score for the user is determined, and based on this score, postural stability assessment for the user is performed.

3 Claims, 4 Drawing Sheets

(51) Int. Cl.
 G16H 50/20 (2018.01)
 G16H 50/30 (2018.01)
(52) U.S. Cl.
 CPC .......... *A61B 5/1128* (2013.01); *A61B 5/4561* (2013.01); *A61B 5/7264* (2013.01); *A61B 5/7267* (2013.01); *G16H 50/20* (2018.01); *G16H 50/30* (2018.01)
(58) Field of Classification Search
 CPC ... A61B 5/1123; A61B 5/7267; A61B 5/1118; A61B 2503/08; G16H 50/30; G16H 50/20
 See application file for complete search history.

(56) References Cited

U.S. PATENT DOCUMENTS

2017/0035330 A1\* 2/2017 Bunn .................... A61B 5/1128
2017/0273601 A1\* 9/2017 Wang .................... A61B 5/4833

OTHER PUBLICATIONS

Cotton, et al. (2009). Statically Equivalent Serial Chains for Modeling the Center of Mass of Humanoid Robots. 138-144. 10.1109/ICHR.2008.4755958. (Year: 2009).\*

Wollseifen, Thomas. "Different methods of calculating body sway area." Pharmaceutical Programming 4.1-2 (2011): 91-106. (Year: 2011).\*

\* cited by examiner

METHOD AND SYSTEM FOR POSTURAL STABILITY ASSESSMENT

PRIORITY CLAIM

This U.S. patent application claims priority under 35 U.S.C. § 119 to: India Application No. 201721024012, filed on 2017 Jul. 7. The entire contents of the aforementioned application are incorporated herein by reference.

TECHNICAL FIELD

This disclosure relates generally to health monitoring and assessment systems, and more particularly to perform postural stability assessment of a user and quantify the assessed postural stability.

BACKGROUND

Postural instability is one of the prominent symptoms associated with geriatric population and in many patients with neurological disorders like stroke, dementia, Parkinson's disease (PD), etc. Postural instability is also the major precursor of fall and about 35% of geriatric population fall each year, making fall prediction a significantly impacting parameter for geriatric health monitoring. Post stroke rehabilitation treatment reveals that about 83% of stroke patients suffer from postural instability leading to high fall risk.

Measurement or quantification of stability is required to estimate severity of stroke, define treatment plan and monitor progress of rehabilitation programs. Postural instability is one of the cardinal signs of PD. The instability leads to progressive reduction in both static and dynamic balance, resulting in recurrent falls.

The inventors here have recognized several technical problems with such conventional systems, as explained below. Most of these postural stability assessment systems are capable of performing the postural stability, however, require manual intervention at different stages of the assessment. Further, the existing systems require service of a trained person to operate the systems and a medically qualified person to interpret outputs. Further, the existing systems in the area of stability assessment work in a static manner by providing a pre-defined questionnaire to the user and by collecting and analyzing user response to the questionnaire.

SUMMARY

Embodiments of the present disclosure present technological improvements as solutions to one or more of the above-mentioned technical problems recognized by the inventors in conventional systems.

For example, in one embodiment, a postural stability assessment system is provided. The system includes a processor; and a memory module comprising a plurality of instructions, the plurality of instructions configured to cause the processor to monitor an action being performed by a user and collecting at least one input pertaining to the action being performed by the user, by an Input/Output (I/O) module of the postural stability assessment system. Further, a SLS duration measurement module of the postural stability assessment system determines a value corresponding to Single Limb Stance (SLS) duration of the user, based on the at least one input. A body joint vibration determination module of the postural stability assessment system then determines a value corresponding to body joint vibration of the user, based on the at least one input. Further, a sway area determination module of the postural stability assessment system determines a value corresponding to body sway area of the user, based on the at least one input. A stability index generation module of the postural stability assessment system then determines the SLS duration, the body joint vibration, and the body sway area, of the user as falling under at least one respective category, and further generates a postural stability index score for the user, based on the determined at least one category of the SLS duration, the body joint vibration, and the body sway area. A stability assessment module of the postural stability assessment system then assesses postural stability of the user, based on the postural stability index score.

In another aspect, a processor-implemented method for postural stability assessment of a user is provided. In this method, in order to perform the postural stability assessment, initially at least one input pertaining to a Single Limb Stance (SLS) duration, body joint vibration, and body sway area, of a user being monitored for postural stability assessment, is collected, via one or more hardware processors, by a postural stability assessment system. Further, the postural stability assessment system determines the SLS duration, the body joint vibration, and the body sway area, of the user as falling under at least one respective category, via the one or more hardware processors. Further, a postural stability index score is generated for the user, based on the determined at least one category of the SLS duration, the body joint vibration, and the body sway area, via the one or more hardware processors, by the postural stability assessment system. Further, postural stability of the user is assessed based on the postural stability index score, by the postural stability assessment system.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Figure 1:
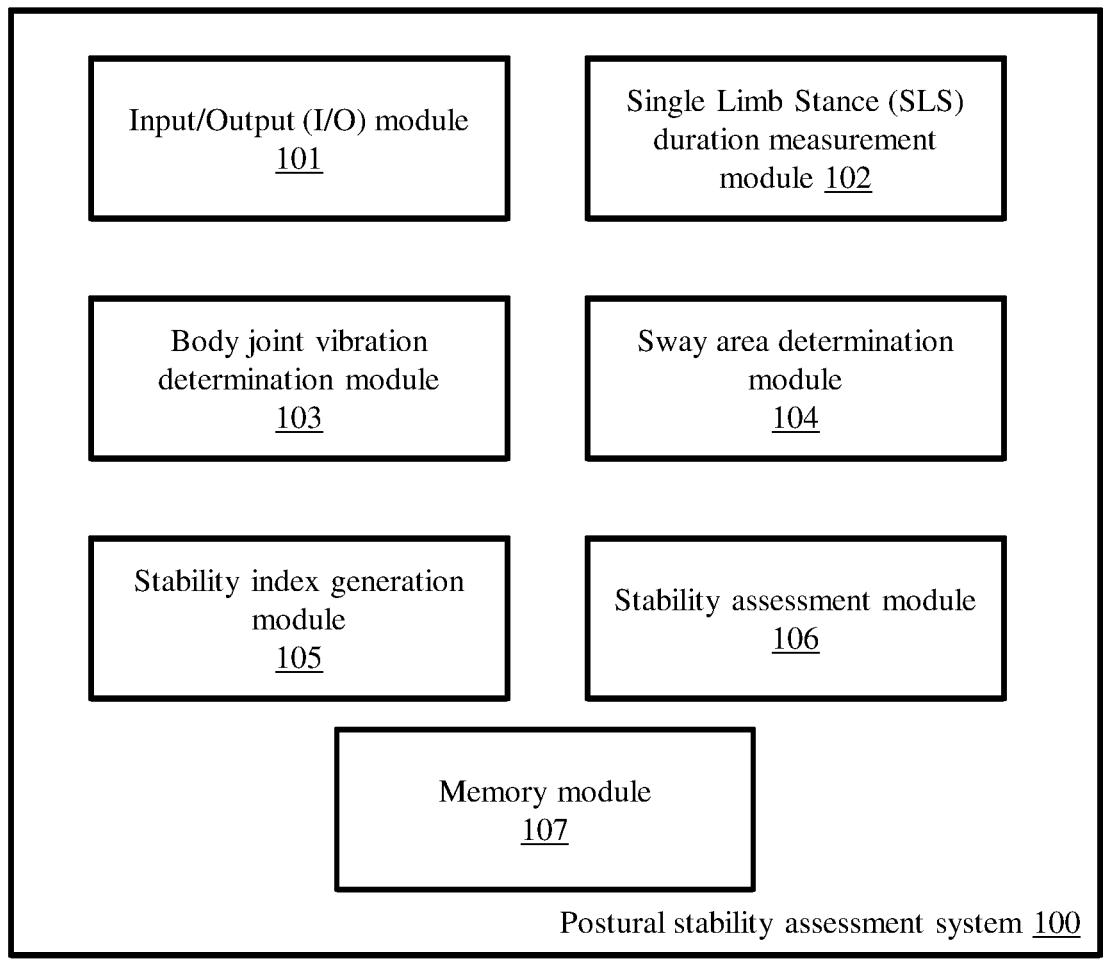
FIG. 1 illustrates an exemplary block diagram of a postural stability assessment system for performing postural stability assessment of a user, according to some embodiments of the present disclosure.

FIG. 1 illustrates an exemplary block diagram of a postural stability assessment system for performing postural stability assessment of a user, according to some embodiments of the present disclosure. The postural stability assessment system 100 includes an Input/Output (I/O) module 101, a Single Limb Stance (SLS) duration measurement module 102, a body joint vibration measurement module 103, a sway area determination module 104, a stability index generation module 105, and a stability assessment module 106.

The I/O module 101 is configured to provide at least a channel with appropriate communication protocol support, for facilitating communication between the postural stability assessment system 100 and at least one external entity. The 'external entity' herein can be a user or an external system. For example, using a suitable interface provided by the I/O module 101, one or more users may interact with the postural stability assessment system 100. In another example, an external system can connect and communicate with the postural stability assessment system 100, for data transfer and/or any such action. The I/O module 101 can be further configured to provide suitable communication channel for communication between the components of the postural stability assessment system 100. The I/O module 101 is further configured to provide suitable options for monitoring action(s) being performed by one or more users, and collect one or more inputs with respect to one or more actions being performed by the user. The I/O module 101 is further configured to collect one or more inputs required for the postural stability assessment, by monitoring the user. For example, the I/O module 101 can use a Kinect® system that is internally or externally associated (or connected) with the postural stability assessment system 100, so as to monitor user action(s) and collect the required input(s). For example, for the purpose of postural stability data assessment, the I/O module 101 can be configured to monitor and record spatio-temporal information of twenty five joints of each user being monitored. The I/O module 101 can be further configured to perform necessary pre-processing of the data collected as input, so as to condition the data for further processing, wherein conditioning of the data refers to preparing the data suitable for further processing (for example, by performing actions such as but not limited to removal of noise content, conversion of the data to appropriate format and so on).

The SLS measurement module 102 is configured to collect the user specific input data from the I/O module 101, process the collected data, and determine SLS time duration for the user. Here, the SLS time duration indicates the time period for which the user being monitored performed the action(s) as required by standard SLS test. For example, SLS time duration is determined by monitoring variation in lifted leg's ankle coordinates. For example, when Kinect® is used for monitoring and data collection, skeleton joints obtained from Kinect® are represented by 3D world co-ordinates (x, y, z) where 'x' represents left/right variation, 'y' represents up/down variation w.r.t ground and 'z' represents to/from variation of subject w.r.t Kinect®. Changes in the lifted leg's ankle y-co-ordinate (say, left leg is lifted) 'YAnkleLeft' can give meaningful information about the precise timing when a subject lifts leg (here, left-leg) above the ground. Similarly right leg's movement also can be tracked.

The body joint vibration determination module 103 is configured to collect the user specific input data collected by the I/O module 101, process the collected data, and determine values that represent one or more types of body joint vibrations while the user was performing one or more specific actions as required for the postural stability assessment. For example, while the user is standing on single limb as part of SLS exercise, the user oscillates in order to maintain the balance. Body joint, especially hip joint contributes maximally to correct the effect of instability to maintain the posture. Acceleration of hip joint center in x, y, z direction is analyzed for estimating body joint vibration. Mean frequencies of the hip joint center were calculated using appropriate techniques such as Fourier transform and the relative frequency variation between each segment of SLS (i.e., double stance, single stance followed by double stance), gives a vibration index.

The sway area determination module 104 is configured to assess body sway from the collected input data, and determine sway of Center of Mass (CoM). Any suitable technique (for example, Statically Equivalent Serial Chain (SESC)) can be used by the sway area determination module 104 for determining the CoM. SESC model locates the CoM of any linkage by means of a serial chain and the links in the chain are defined by their geometric configuration and mass distribution. Shoulder center and hip center are considered as the start and end point of the serial chain respectively. Midpoint of this chain is estimated to be the body CoM, and projection of the estimated CoM is equivalent to body sway. The sway area can be calculated using any suitable algorithm. For example, a convex hull algorithm can be used. In the convex hull method triangulation of the point sets is calculated first. The points of interest are the x and z coordinates of estimated CoM. These coordinates (x1; z1)::: (xn; Zn) of the polygon are arranged in a determinant, and cross product of the determinant generates the sway area.

The stability index generation module 105 is configured to collect information pertaining to the determined SLS time duration, body joint vibration, and sway area, and process them together to generate a postural stability index score, wherein the postural stability index score represents level of postural stability of the user, and can further indicate any potential health risks. The stability index generation module 105 processes information pertaining to the SLS time duration, body joint vibration, and sway area, based on certain pre-defined rules. During this process, the stability index generation module 105 compares determined values of the SLS time duration, body joint vibration, and sway area with corresponding membership function ranges, and accordingly determines one membership function each that suits the determined value of each parameter. Here, 'membership function' refers to classifications each of SLS time duration, body joint vibration, and sway area under different categories (wherein each category is defined in terms of range of values).

SLS duration: Poor: 8 to 25 sec, Average: 20 to 40 sec, Good: 35-85 sec, Excellent: 80 to 120 sec.

Body (Hip) Joint vibration: Poor: 0 to 5, Average: 5 to 15, Good: 15 to 35, Excellent: 30 to 50.

CoM sway area: Poor: 16 to 25; Average: 8 to 16; Good: 4 to 8; Excellent: 0 to 4.

In an embodiment, the stability index generation module 105 dynamically determines the ranges for a person being analyzed. The stability index generation module 105 may consider the parameters such as but not limited to age of the user, geographical location of the user and so on, that has impact on physical health of a user, in order to dynamically determine the ranges, and compare values corresponding to such features with a learning model that specifies criteria for selecting the ranges. By comparing the value of each parameter with corresponding membership function ranges, the stability index generation module 105 determines the matching membership functions for the user. The means, each of SLS duration, body joint vibration, and sway area are classified as one of GOOD, BAD, AVERAGE, EXCELLENT. In another embodiment, the stability index generation module 105 dynamically determines the range of membership functions for a user, based on one or more diseases the user has. For example, ranges of membership functions for all users suffering from stroke. Similarly, for all users suffering from another particular disease, the range would be a different set of values. In this scenario, information pertaining to one or more diseases a user is suffering from, is collected as one of the inputs, by the stability index generation module 105, through the I/O module 101, for the purpose of determining the range of membership functions for the user. Similarly Neurological balance disorders like stroke, dementia etc., musculoskeletal balance disorders like arthritis and geriatric care. These membership functions are then combined with rules to generate the postural stability score. In an embodiment, any suitable technique (for example, Fuzzy logic) can be used to combine the membership functions and the rules. A few examples of the rules used are:

Rule 1: IF SLS duration is EXCELLENT; AND vibration index is GOOD; AND sway area is GOOD; THEN stability is EXCELLENT (score-75 to 100)

Rule 2: IF SLS duration is Good; AND vibration index is Average; AND sway area is GOOD; THEN stability is Good (score-50 to 75)

Rule 3: IF SLS duration is AVERAGE; AND vibration index is GOOD; AND sway area is AVERAGE; THEN stability is AVERAGE (score-25 to 50)

Rule 4: IF SLS duration is POOR; AND vibration index is POOR; AND sway area is AVERAGE; THEN stability is POOR (score-0 to 25)

Using the combination of membership functions and the rules the postural stability index score for the user is determined. Value of the postural stability index score, as determined, is then provided as input to the stability assessment module 106. The stability assessment module 106 can be configured to interpret the postural stability index score received as input, and generate appropriate suggestions/recommendations which are then provided as output to the user. In an embodiment, the interpretation of the postural stability index score is performed by the stability assessment module 106, on the basis of information that is statically or dynamically configured. For example, if the value of the postural stability index score is 20, then the stability is POOR, and the user may be recommended appropriate medical checkup and the like.

The memory module 107 can be configured to store any data that is associated with the postural stability assessment. In an embodiment, the information pertaining to membership functions of different parameters for a user or for a particular population, statically or dynamically decided, is stored in the memory module 107. Similarly all rules that are to be used for performing the postural stability assessment also are stored in the memory module 107. Further, all information (inputs, outputs and so on) pertaining to postural stability assessment performed for each user may also be stored in the database, as history data, for reference purpose. The learning model also is stored in the memory module 107. The memory module 107 may be volatile or non-volatile, as per requirements.

Figure 2:
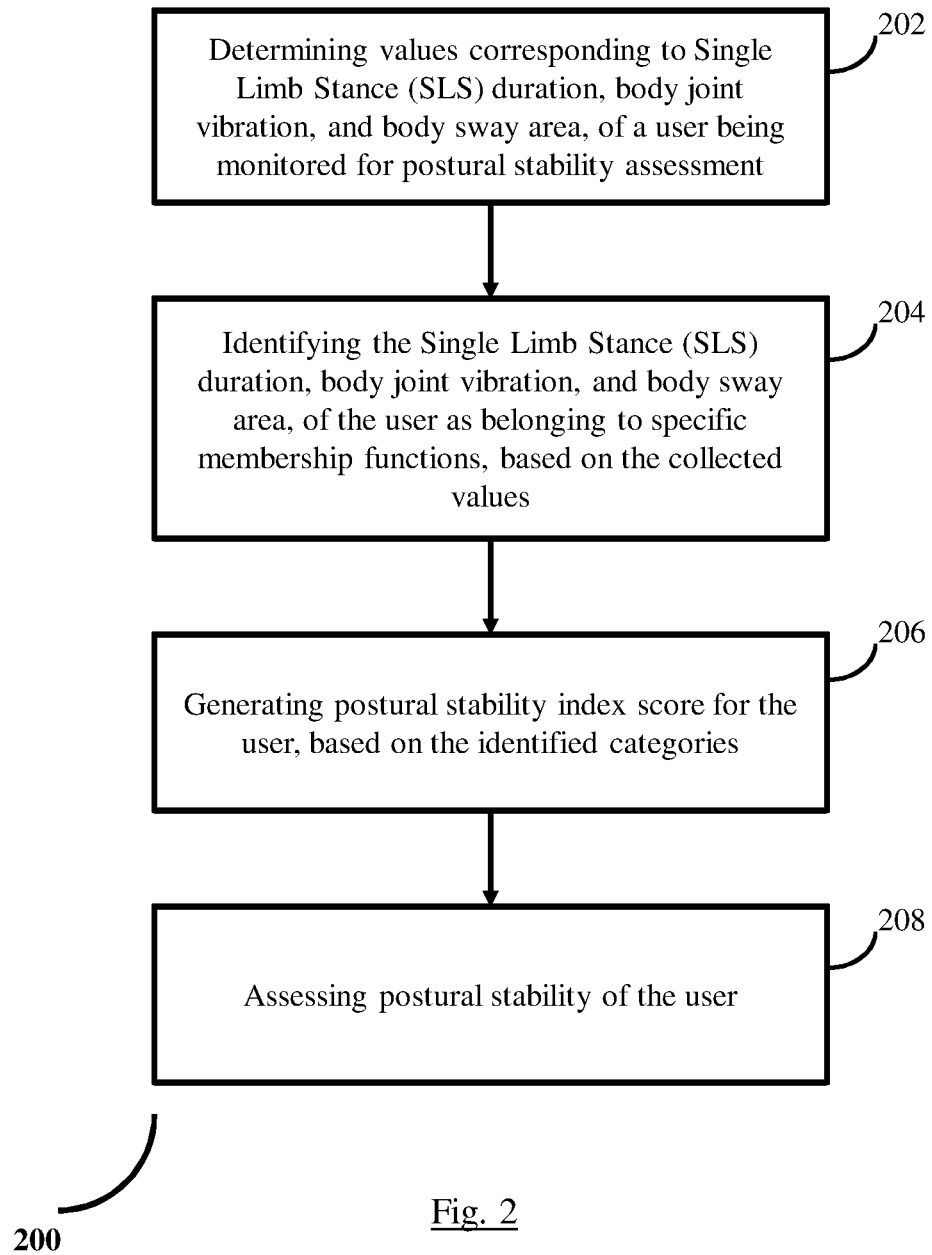
FIG. 2 is a flow diagram depicting steps involved in the process of performing postural stability assessment, using the postural stability assessment system, according to some embodiments of the present disclosure.

FIG. 2 is a flow diagram depicting steps involved in the process of performing postural stability assessment, using the postural stability assessment system, according to some embodiments of the present disclosure. By monitoring a user for whom the posture stability assessment is to be performed, while the user is performing specific (manual) actions that are required for the postural stability assessment (SLS test for instance) required inputs are collected which can be further used for the assessment.

The input(s) thus collected is then processed by the postural stability assessment system 100 to determine (202) values that represent SLS duration, body joint vibration, and body sway area, for the user. The identified values are further processed by the postural stability assessment system 100 to identify (204) these values as belonging to (or matching) specific membership functions. The postural stability assessment system 100 further generates (206) a postural stability index score for the user, based on the identified membership functions and at least one rule. The postural stability assessment system 100 further assesses postural stability of the user, based on the generated postural stability index score. Various actions in FIG. 2 can be performed in the same order or in a different order. Further, or one or more of the actions in method 200 can be omitted.

Figure 3:
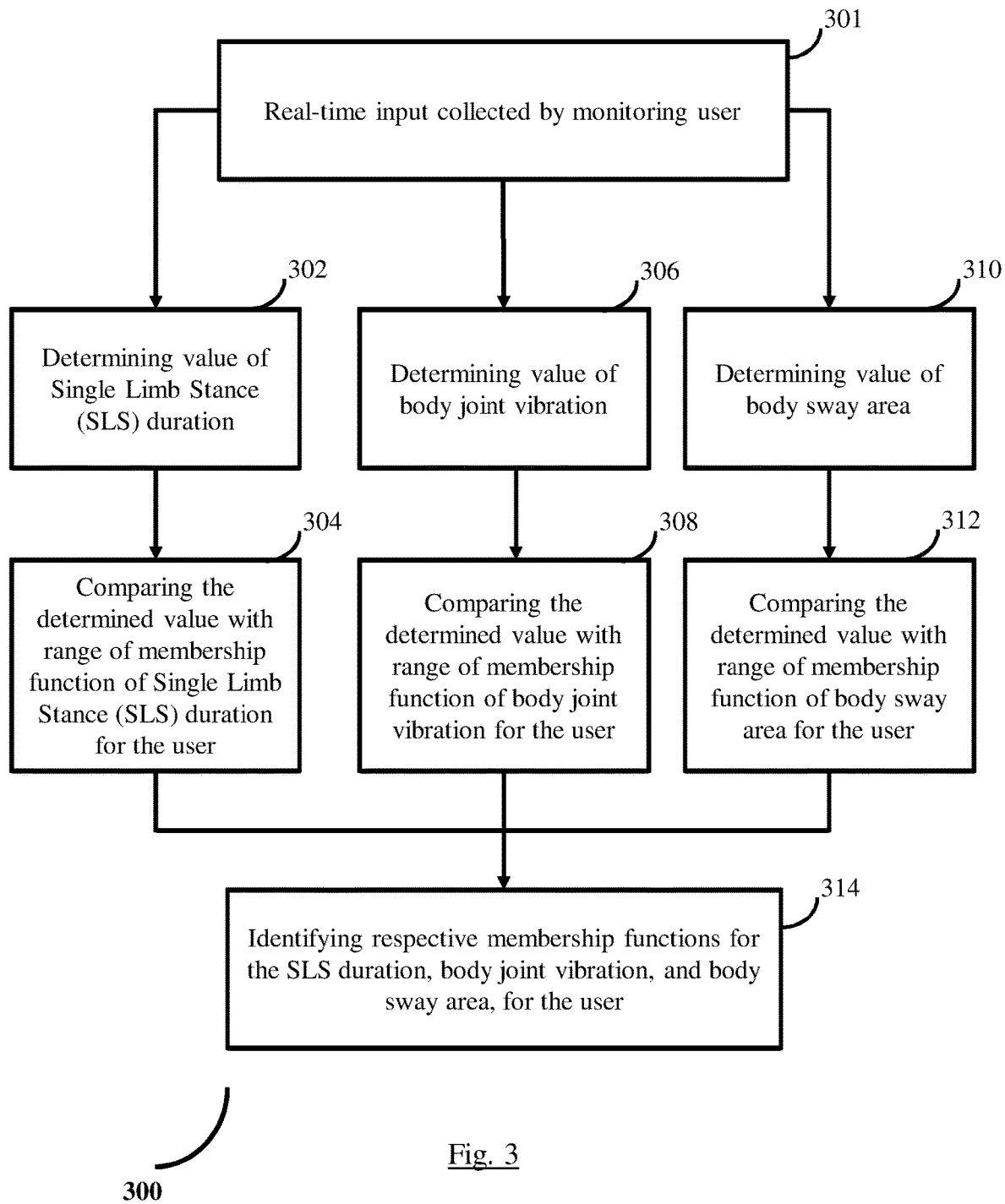
FIG. 3 is a flow diagram depicting steps involved in the process of identifying membership function for SLS duration, body joint vibrations, and body sway area of a user being monitored, using the postural stability assessment system, according to some embodiments of the present disclosure.

FIG. 3 is a flow diagram depicting steps involved in the process of identifying membership function for SLS duration, body joint vibrations, and body sway area of a user being monitored, using the postural stability assessment system, according to some embodiments of the present disclosure. The postural stability assessment system 100 determines values of SLS duration, body joint vibration, and CoM of body sway area (302, 306, and 310 respectively), by processing the real-time inputs collected (301) by monitoring the user. The values thus determined are then compared (304, 308, 312 respectively) with respective membership function ranges, wherein the ranges of membership function of each of the SLS duration, the body joint vibration, and the CoM of body sway area are dynamically determined for the user, by the postural stability assessment system 100. By means of the comparison, the postural stability assessment system 100 identifies (314) membership function that matches each of the SLS duration, the body joint vibration, and the CoM of body sway area, for the user. Various actions in FIG. 3 can be performed in the same order or in a different order. Further, or one or more of the actions in method 300 can be omitted.

Figure 4:
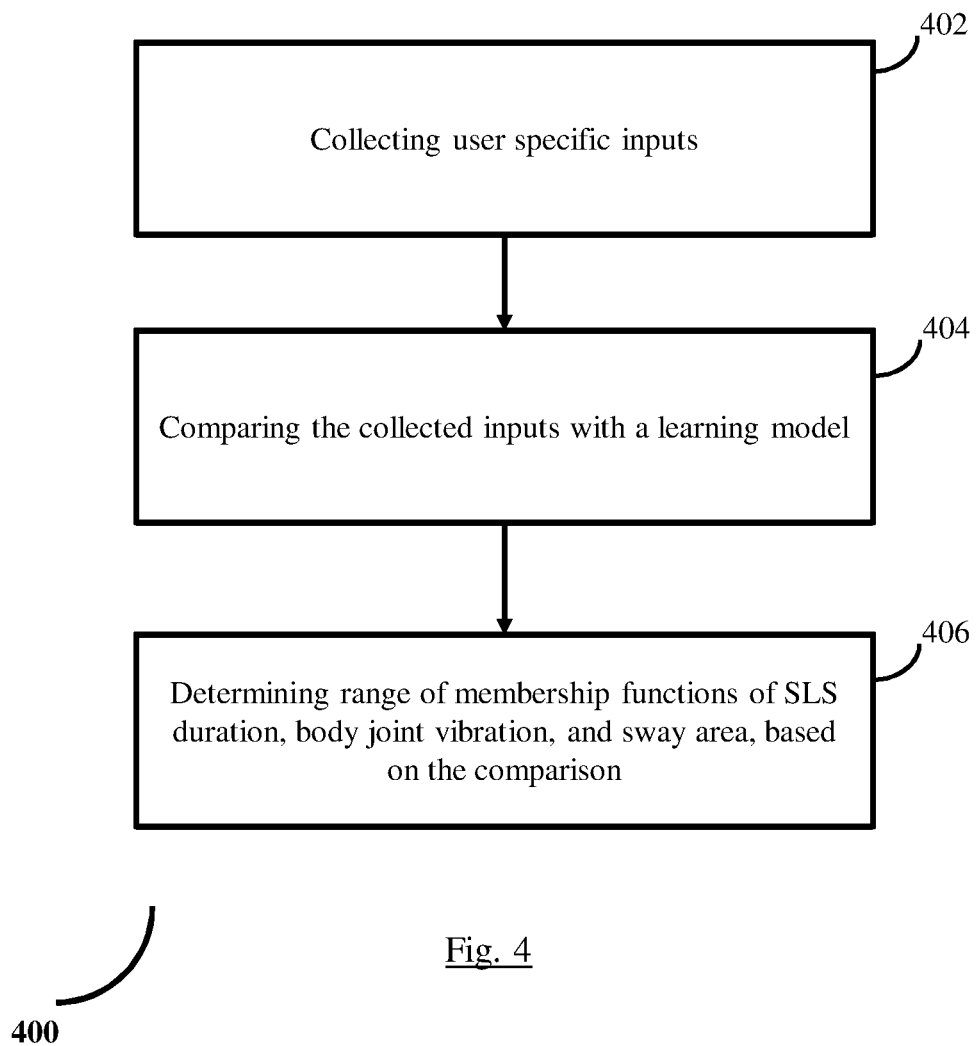
FIG. 4 is a flow diagram depicting steps involved in the process of dynamically determining range of membership functions of SLS duration, body joint vibrations, and body sway area of a user, using the postural stability assessment system, according to some embodiments of the present disclosure.

FIG. 4 is a flow diagram depicting steps involved in the process of dynamically determining range of membership functions of SLS duration, body joint vibrations, and body sway area of a user, using the postural stability assessment system, according to some embodiments of the present disclosure. The postural stability assessment system 100 collects (402) user specific parameters such as but not limited to age of the user, geographical location of the user and so on, as inputs for dynamically determining ranges of membership functions for the user. These values are then compared (404) with a learning model that specifies criteria for selecting the ranges. Once a matching criteria is found, the ranges of membership functions mapped against that particular criteria are selected as the ranges of membership functions for the user. Various actions in FIG. 4 can be performed in the same order or in a different order. Further, or one or more of the actions in method 400 can be omitted.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for postural stability assessment of a user, said method comprising:

collecting spatio-temporal information of joints of a user through an input/output module via one or more hardware processors of a postural stability assessment system connected to a real-time motion sensor, the spatio-temporal information pertaining to a Single Limb Stance (SLS) duration, body joint vibration, and body sway area, wherein the spatio-temporal information of joints is associated with one or more actions performed by the user being monitored for postural stability assessment, wherein the real-time motion sensor monitors the one or more actions performed by the user and collect one or more real-time inputs, wherein the spatio-temporal information of joints is collected by processing the real-time inputs of 3-D world co-ordinates (x, y, z) of the joints obtained from the real-time motion sensor, where 'x' represents left or right variation, 'y' represents up or down variation with respect to a ground and 'z' represents to or from variation of the user, wherein the SLS duration is determined by monitoring a change in lifted leg's ankle y-coordinates in the real-time inputs to get precise timing on when the user lifts one-leg above the ground and also track movement of another leg of the user, and wherein the body joint vibration is determined by monitoring an acceleration of hip joint center in x, y, z direction in the real-time inputs;

assessing, via the one or more hardware processors, a sway of Center of Mass (CoM) from the spatio-temporal information of joints of the user using a Statistically Equivalent Serial Chain (SESC) that locates the CoM of any linkage by means of serial chain and links in the serial chain are defined by their geometric configuration and mass distribution, wherein a shoulder center and a hip center are considered as a start point and an end point of the serial chain, respectively, wherein a midpoint of the serial chain is estimated to be the CoM, and a projection of the estimated CoM is equivalent to a body sway, and wherein the body sway area is calculated using a convex hull algorithm over the sway of CoM;

determining, via the one or more hardware processors, membership functions by classification of each of the SLS duration, the body joint vibration, and the body sway of all users into categories of good, bad, average, excellent, wherein each of the categories is defined in terms of a range of values, wherein the ranges of the membership functions are determined based on one or more diseases all the users have by:

collecting values for parameters having impact on the users' health; and determining the ranges for the membership functions of the SLS duration, the body joint vibration, and the body sway area, that match the collected values of the parameters;

determining the SLS duration, the body joint vibration, and the body sway area, of said user as falling under at least one of the categories, via the one or more hardware processors, by comparing values of the SLS duration, the body joint vibration, and the body sway area of said user with the ranges of the membership functions based on one or more diseases the user is suffering from;

dynamically generating a postural stability index score for said user, based on said determined categories of the SLS duration, the body joint vibration, the body sway area, and one or more rules, via the one or more hardware processors, wherein the postural stability index score is generated by combining the range of membership functions of the SLS duration, the body joint vibration, and the body sway area using Fuzzy logic technique based on the one or more rules, wherein the rule comprises determining if the SLS duration is excellent, and the vibration index is good, and the sway area is good, then the postural stability index score is 75 to 100; and automatically assessing, via the one or more hardware processors, postural stability of said user, by interpreting the postural stability index score, and providing recommendation of medical check up as output to the user, wherein the postural stability index score represents a level of postural stability of the user and indicate potential health risks.

2. A postural stability assessment system, said system comprising:
a processor; and
a memory module comprising a plurality of instructions, said plurality of instructions configured to cause the processor to:
monitor spatio-temporal information of joints of a user, associated with one or more actions being performed by the user and collecting the spatio-temporal information of joints of the user, by an Input/Output (I/O) module via one or more hardware processors of the postural stability assessment system connected to a real-time motion sensor that monitors the one or more actions performed by the user and collect one or more real-time inputs;
determine a value corresponding to Single Limb Stance (SLS) duration of the user, based on the spatio-temporal information, by a SLS duration measurement module of the postural stability assessment system;
determine a value corresponding to body joint vibration of the user, based on the spatio-temporal information, by a body joint vibration determination module of the postural stability assessment system;
determine a value corresponding to body sway area of the user, based on the spatio-temporal information, by a sway area determination module of the postural stability assessment system;
wherein the spatio-temporal information of joints is collected by processing real-time inputs of 3-D world co-ordinates (x, y, z) of the joints obtained from the real-time motion sensor, where 'x' represents left/right variation, 'y' represents up/down variation with respect to a ground and 'z' represents to/from variation of subject,
wherein the SLS duration is determined by monitoring a change in lifted leg's ankle y-coordinates in the real-time inputs to get precise timing on when the user lifts one-leg above the ground and also track movement of another leg of the user, and
wherein the body joint vibration is determined by monitoring an acceleration of hip joint center in x, y, z direction in the real-time inputs,
assess a sway of Center of Mass (CoM) from the spatio-temporal information of joints of the user using a Statistically Equivalent Serial Chain (SESC) that locates the CoM of any linkage by means of serial chain and links in the serial chain are defined by their geometric configuration and mass distribution, wherein a shoulder center and a hip center are considered as a start point and an end point of the serial chain, respectively, wherein a midpoint of the serial chain is estimated to be the CoM, and a projection of the estimated CoM is equivalent to a body sway, and wherein the body sway area is calculated using a convex hull algorithm over the sway of CoM;
determine membership functions by classification of each of the SLS duration, the body joint vibration, and the body sway of all users into categories of good, bad, average, excellent, wherein each of the categories is defined in terms of a range of values, wherein the ranges of the membership functions are determined based on one or more diseases all the users have by:
collecting values for parameters having impact on the users' health; and
determining the ranges for the membership functions of the SLS duration, the body joint vibration, and the body sway area, that match the collected values of the parameters;
determine the SLS duration, the body joint vibration, and the body sway area, of said user as falling under at least one of the categories, by comparing values of the SLS duration, the body joint vibration, and the body sway area of said user with the ranges of the membership function based on one or more diseases the user is suffering from;
dynamically generate a postural stability index score for said user, based on said determined categories of the SLS duration, the body joint vibration, the body sway area, and one or more rules, by a stability index generation module, wherein the postural stability index score is generated by combining the range of membership functions of the SLS duration, the body joint vibration, and the body sway area using Fuzzy logic technique based on the one or more rules, wherein the rule comprises determining if the SLS duration is excellent, and the vibration index is good, and the sway area is good, then the postural stability index score is 75 to 100; and
automatically assess, via the one or more hardware processors, postural stability of said user, by interpreting the postural stability index score, by a stability assessment module of the postural stability assessment system, and providing recommendations of medical check up as output to the user via the Input/Output (I/O) module, wherein the postural stability index score represents a level of postural stability of the user and indicate potential health risks.

3. One or more non-transitory machine readable information storage mediums comprising one or more instructions which when executed by one or more hardware processors causes:
collecting spatio-temporal information of joints of a user through an input/output module of a postural stability assessment system connected to a real-time motion sensor, the spatio-temporal information pertaining to a Single Limb Stance (SLS) duration, body joint vibration, and body sway area, wherein the spatio-temporal information of joints is associated with one or more actions performed by the user being monitored for postural stability assessment, wherein the real-time motion sensor monitors the one or more actions performed by the user and collect one or more real-time inputs,
wherein the spatio-temporal information of joints is collected by processing real-time inputs of 3-D world co-ordinates (x, y, z) of the joints obtained from the real-time motion sensor, where 'x' represents left/right variation, 'y' represents up/down variation with respect to a ground and 'z' represents to/from variation of subject,
wherein the SLS duration is determined by monitoring a change in lifted leg's ankle y-coordinates in the real-time inputs to get precise timing on when the user lifts one-leg above the ground and also track movement of another leg of the user, and
wherein the body joint vibration is determined by monitoring an acceleration of hip joint center in x, y, z direction in the real-time inputs;
assessing, via the one or more hardware processors, sway of Center of Mass (CoM) from the spatio-temporal information of joints of the user using a Statistically Equivalent Serial Chain (SESC) that locates the CoM of any linkage by means of serial chain and links in the serial chain are defined by their geometric configuration and mass distribution, wherein a shoulder center and a hip center are considered as a start point and an end point of the serial chain, respectively, wherein a midpoint of the serial chain is estimated to be the CoM, and a projection of the estimated CoM is equivalent to a body sway, and wherein the body sway area is calculated using a convex hull algorithm over the sway of CoM;

determining, via the one or more hardware processors, membership functions by classification of each of the SLS duration, the body joint vibration, and the body sway of all users into categories of good, bad, average, excellent, wherein each of the categories is defined in terms of a range of values, wherein the ranges of the membership functions are determined based on one or more diseases all the users have by:
    collecting values for parameters having impact on the users' health; and
    determining the ranges for the membership functions of the SLS duration, the body joint vibration, and the body sway area, that match the collected values of the parameters;

determining the SLS duration, the body joint vibration, and the body sway area, of said user as falling under at least one of the categories, via the one or more hardware processors, by comparing values of the SLS duration, the body joint vibration, and the body sway area of said user with the ranges of the membership functions based on one or more diseases the user is suffering from;

dynamically generating a postural stability index score for said user, based on said determined categories of the SLS duration, the body joint vibration, the body sway area, and one or more rules, via the one or more hardware processors, wherein the postural stability index score is generated by combining the range of membership functions of the SLS duration, the body joint vibration, and the body sway area using Fuzzy logic technique based on the one or more rules, wherein the rule comprises determining if the SLS duration is excellent, and the vibration index is good, and the sway area is good, then the postural stability index score is 75 to 100; and automatically assessing, via the one or more hardware processors, postural stability of said user, by interpreting the postural stability index score, and providing recommendation of medical check up as output to the user, wherein the postural stability index score represents a level of postural stability of the user and indicate potential health risks.

\* \* \* \* \*